(12) United States Patent
Frey, II et al.

(10) Patent No.: US 11,013,873 B2
(45) Date of Patent: May 25, 2021

(54) METHODS FOR TREATING PATIENTS WITH IMPAIRED AWARENESS OF HYPOGLYCEMIA

(71) Applicant: HealthPartners Institute, Bloomington, MN (US)

(72) Inventors: William H. Frey, II, St. Paul, MN (US); Richard M. Bergenstal, Plymouth, MN (US); Leah R. Bresin Hanson, Vadnais Heights, MN (US); Anders L. Carlson, Minneapolis, MN (US)

(73) Assignee: HealthPartners Institite, Bloomington, MN (US)

( * ) Notice: Subject to any disclaimer, the term of this patent is extended or adjusted under 35 U.S.C. 154(b) by 17 days.

(21) Appl. No.: 15/861,853

(22) Filed: Jan. 4, 2018

(65) Prior Publication Data
US 2018/0193576 A1    Jul. 12, 2018

Related U.S. Application Data

(60) Provisional application No. 62/443,004, filed on Jan. 6, 2017.

(51) Int. Cl.
*A61K 38/28* (2006.01)
*A61M 15/08* (2006.01)
*A61K 9/00* (2006.01)

(52) U.S. Cl.
CPC .......... *A61M 15/08* (2013.01); *A61K 9/0073* (2013.01); *A61K 38/28* (2013.01); *A61K 9/0019* (2013.01); *A61K 9/0043* (2013.01)

(58) Field of Classification Search
CPC ............................... A61M 15/08; A61K 38/28
See application file for complete search history.

(56) References Cited

U.S. PATENT DOCUMENTS

| | | | | |
|---|---|---|---|---|
| 7,642,232 B2 * | 1/2010 | Green | ................. | A61K 38/28 514/1.1 |
| 10,188,739 B2 * | 1/2019 | Jain | .................. | A61K 38/28 |
| 10,213,487 B2 * | 2/2019 | Mantripragada | ...... | A61K 38/26 |
| 2006/0160722 A1 * | 7/2006 | Green | ................... | A61K 38/26 514/5.9 |
| 2006/0239934 A1 * | 10/2006 | Cheatham | ............ | A61K 9/0073 424/46 |
| 2014/0255384 A1 | 9/2014 | Frey, II | | |
| 2015/0283065 A1 | 10/2015 | Frey, II et al. | | |

OTHER PUBLICATIONS

Fanelli et al., Long-Term Recovery from Unawareness, deficient counterregulation and lack of cognitive dysfunction during hypoglycemia, following institution of rational, intensive insulin therapy in IDDM in Diabetologia, 1994. vol. 37, pp. 1265-1276, p. 1265, col., para 1 to col. 2, para 2.
McCall et al., Insulin Therapy and Hypoglycemia in Endocrinol Metab Clin N. Am. 2012, vol. 41, p. 57-87. Entire Document.
Senstius et al., "Comparison of In Vitro Stability for Insulin Aspart and Insulin Glulisine During Simulated Use in Infusion Pumps in Diabetes Technology and Therapeutics", 2007, vol. 9, pp. 517-521. p. 518, Table.
International Search Report and Written Opinion, dated Mar. 23, 2018, for PCT Application No. PCT/US18/12447, filed Jan. 5, 2018.
International Preliminary Report on Patentability issued in related PCT application No. PCT/US2018/12447, dated Jul. 18, 2019.

* cited by examiner

*Primary Examiner* — Gyan Chandra

(74) *Attorney, Agent, or Firm* — Barnes & Thornburg LLP; Jeffrey R. Stone

(57) ABSTRACT

The present system is directed in one embodiment to a method of administration of a therapeutic composition for treatment, prevention and/or mitigation of the frequency and/or severity of impaired awareness of hypoglycemia (IAH). The method includes administering one or more therapeutic agent(s) or composition(s) comprising insulin to the upper third of a patient's nasal cavity, thereby delivering the therapeutic composition directly to the patient's central nervous system for treatment, prevention and/or mitigation of the frequency and/or severity of IAH. In still another embodiment, the therapeutic composition comprises a non-zinc containing form of insulin.

11 Claims, No Drawings

METHODS FOR TREATING PATIENTS WITH IMPAIRED AWARENESS OF HYPOGLYCEMIA

CROSS-REFERENCE TO RELATED APPLICATIONS

The present application claims priority to provisional application No. 62/443,004, filed on Jan. 6, 2017 and entitled TREATMENT OF HYPOGLYCEMIA UNAWARENESS WITH INTRANASAL INSULIN, the entire contents of which are incorporated herein by reference.

BACKGROUND OF THE INVENTION

Field of the Invention

The present disclosure generally relates to methods of treating and preventing impaired awareness of hypoglycemia in humans. More particularly, the present disclosure is directed to a method of treating and preventing impaired unawareness of hypoglycemia by administration of intranasal insulin to the upper one-third of a patient's nasal cavity.

Description of the Related Art

Currently hypoglycemia, or the fear of it, is one of the most significant limits to current management of type I diabetes (T1D). Hypoglycemia occurs with high frequency among patients with T1D, with a frequency of mild hypoglycemia at 1 to 2 events per patient per week and severe hypoglycemia (requiring assistance from another person) at 0.2 to 0.3 events per patient per year. With repeated episodes of hypoglycemia, the counter-regulatory pathways to restore normal glucose are blunted, and patients can, as a result, become unaware of the hypoglycemia.

Thus, impaired awareness of hypoglycemia ("IAH") also known as hypoglycemia unawareness, may comprise a complication of diabetes in which the patient is unaware of a steep drop in blood sugar. In these cases, there is a failure to trigger the secretion of epinephrine which, when secreted, generates the characteristic symptoms of hypoglycemia, e.g., palpitations, sweating, anxiety that serve to warn the patient of dropping blood glucose levels.

IAH can result in prolonged exposure to hypoglycemic conditions, leading to, e.g., seizures, loss of consciousness and/or brain damage and in some case may be fatal. The development of IAH also makes intensified blood glucose control more difficult and puts the patient at risk for severe hypoglycemia-related conditions.

It is estimated that 40% of patients with T1D have IAH. Patients at risk for IAH have one or more of the following characteristics; long-standing T1D; intensive therapy at an advanced age, and/or a history of frequent hypoglycemia; neuropathy or damage to the parts of the nervous system that trigger the body's response to low blood sugars; strict blood sugar control and on an intensive insulin regimen, have a history of low blood sugar requiring aid from another person and/or recent low blood sugar; taking drugs for heart or high blood pressure that may mask the body's response to low blood sugar.

It is also known that patients with Type 2 diabetes can also have IAH, though it is less common.

Further, it is known that intranasal administration of therapeutic compounds or agents may, in some cases, increase the effectiveness of certain therapeutic compounds or agents in bypassing the blood brain barrier (BBB) and delivering the compound or agent directly to the CNS. Thus, intranasal administration of therapeutic compounds may allow increased prevention and/or treatment of certain diseases or conditions.

It is also known that greater than 98% of small molecule and nearly 100% of large molecule CNS drugs developed by the pharmaceutical industry do not cross the BBB. Intracerebroventricular or intraparenchymal drug administration can directly deliver therapeutics to the brain; however, these methods are invasive, inconvenient, and impractical for the numbers of individuals requiring therapeutic interventions for treating CNS disorders. Intranasal drug administration to the upper one-third of the patient's nasal cavity is a noninvasive and convenient means to rapidly target therapeutics of varying physical and chemical properties to the CNS. The olfactory and trigeminal neural pathways connecting the nasal passages to the CNS are clearly involved in the delivery of therapeutic compounds applied via intranasal administration to the upper third of the nasal cavity. In addition to these neural pathways, perivascular pathways, and pathways involving the cerebrospinal fluid or nasal lymphatics may play a central role in the distribution of therapeutics from the nasal cavity to the CNS.

The general intranasal method of drug delivery, i.e., administration to the lower two-thirds of the patient's nasal cavity, holds great promise as an alternative to more invasive routes, however, a number of factors limit the efficiency of general intranasal delivery to the CNS. Absorption of intranasally applied drugs into the capillary network in the nasal mucosa can decrease the amount of drug available for direct transport into the CNS. Additional factors within the nasal cavity, including the presence of nasal mucociliary clearance mechanisms, metabolizing enzymes, efflux transporters and nasal congestion can also reduce the efficiency of delivery into the CNS. In particular, therapeutic compounds may be absorbed into the blood and/or delivered to peripheral (non-target) tissues, thus reducing delivery of the compound to the target. As a result, the efficacy of administering therapeutic compounds to the lower two-thirds of the nasal cavity with the goal of delivering therapeutics to the CNS is greatly diminished. Further, the efficacy of administering therapeutic compounds to the upper one-third of the nasal cavity as a means to target therapeutics to the CNS could also be improved.

The method of administration of insulin to the upper one-third of the nasal cavity for treatment of neurodegenerative disorders, specifically Alzheimer's disease, provides the foundational basis for the present invention. Insulin has been shown to improve memory in healthy adults, with no change in blood levels of insulin or glucose. See, e.g., Benedict C., et al (2004), Intranasal insulin improves memory in humans, Psychoneuroendocrinology, 29:1326-1334; Craft (2012), Alzheimer disease: Insulin resistance and AD—Extending the translational path. Nat Rev Neurol. 8:360-362; Reger et al., (2006), Effects of intranasal insulin on cognition in memory in memory-impaired older adults: Modulation by APOE genotype. Neurobiol Aging. 27:451-458; Reger, et al. (2008), Intranasal insulin improves cognition and modulates beta-amyloid in early AD, Neurology. 70-440-448.

Insulin is known to be an effective treatment of Alzheimer's disease because glucose uptake and use are significantly decreased in patients with Alzheimer's disease. See de Leon, et al., (1997), Cortisol reduces hippocampal glucose metabolism in normal elderly, but not in Alzheimer's disease. J Clin Endocrinol Metab., 82:3251-3269. Glucose is the only source of energy used by brain cells under normal conditions, and the brain cells of patients with Alzheimer's disease are starved for energy. Alzheimer's disease has been reported to involve a deficiency of insulin and insulin signaling in the brain.

It would be desirable to provide a method of preventing and/or treating IAH by directly delivering an effective amount of insulin to the target within the patient's CNS for rapid uptake and utilization. In the case of IAH, the steep drop in glucose levels demands the fastest and most targeted treatment possible which, in many cases, requires the patient be aware of the hypoglycemic event. It would also be desirable to reduce absorption of intranasally-administered therapeutic compounds or agents, in this case insulin, for prevention and treatment of IAH, into the blood and delivery to non-target or peripheral tissues. It would be further desirable to provide an intranasal delivery method and pharmaceutical composition(s) that are effective and efficient in facilitating delivery, and maximum efficiency of delivery, of therapeutic compounds, e.g., insulin, to the CNS.

The present invention addresses, inter alia, these issues.

BRIEF SUMMARY OF THE INVENTION

The present system is directed in one embodiment to a method of administration of a therapeutic composition for treatment, prevention and/or mitigation of the frequency and/or severity of impaired awareness of hypoglycemia (IAH). The method includes administering one or more therapeutic agent(s) or composition(s) comprising insulin to the upper third of a patient's nasal cavity, thereby delivering the therapeutic composition directly to the patient's central nervous system for treatment, prevention and/or mitigation of the frequency and/or severity of IAH. In still another embodiment, the therapeutic composition comprises a non-zinc containing form of insulin.

In still another embodiment, the insulin formulation is preserved with pyrophosphate or one of its analogues and may be prepared as a unit dose. In still another embodiment, the non-zinc containing insulin is formulated as a unit does that does not contain a cresol or a phenol preservative.

An object of the present invention comprises administering an effective amount of insulin to the upper third of a patient's nasal cavity, thereby enabling the effective amount of insulin to bypass the patient's blood-brain barrier, thus directly delivering the effective amount of insulin to the patient's CNS, i.e., brain for the prevention and/or treatment of IAH in the patient. Stated differently, an object of the present invention is to create an awareness of hypoglycemia in the patent with IAH so they may recognize the hypoglycemia and take appropriate action.

Accordingly, further objects of the present invention comprise reducing, preventing and/or mitigating the severity of IAH in patients.

The figures and the detailed description which follow more particularly exemplify these and other embodiments of the invention.

BRIEF DESCRIPTION OF THE DRAWINGS

The invention may be more completely understood in consideration of the following detailed description of various embodiments of the invention in connection with the accompanying FIGURES and Tables included herein.

DETAILED DESCRIPTION OF THE INVENTION, INCLUDING THE BEST MODE

While the invention is amenable to various modifications and alternative forms, specifics thereof are shown by way of example in the drawings and described in detail herein. It should be understood, however, that the intention is not to limit the invention to the particular embodiments described. On the contrary, the intention is to cover all modifications, equivalents, and alternatives falling within the spirit and scope of the invention.

DEFINITIONS

As used herein, "central nervous system" (CNS) refers to the brain and spinal cord and associated tissues.

As used herein, "drug targeting" refers to increasing drug concentration in a tissue relative to the concentration of that drug in the blood.

As used herein, "efficiency" refers to targeting specificity of the drug, i.e., therapeutic compound to a particular physiological location, delivery with minimal residual loss to non-target physiological locations, or both.

As used herein, "meninges" refers to the dura, pia and arachnoid membranes surrounding the brain and spinal cord.

As used herein, "brainstem" refers to the pons, medulla and midbrain.

An "effective amount" of therapeutic compound or agent such as insulin is an amount sufficient to prevent, treat, reduce and/or ameliorate the symptoms, neuronal damage and/or underlying causes of any of the referenced disorders or diseases. In some instances, an "effective amount" is sufficient to eliminate the symptoms of those diseases and, perhaps, overcome the disease itself.

In the context of the present invention, the terms "treat" and "therapy" and "therapeutic" and the like refer to alleviate, slow the progression, prophylaxis, attenuation or cure the condition(s) resulting from IAH.

"Prevent", as used herein, refers to putting off, delaying, slowing, inhibiting, or otherwise stopping, reducing or ameliorating the onset of conditions related to hypoglycemia unawareness or other CNS-related disease and/or condition. It is preferred that a large enough quantity of the agent be applied in non-toxic levels in order to provide an effective level of neuroprotection. The method of the present invention may be used with any animal, such as a mammal or a bird (avian), more preferably a mammal. Poultry are a preferred bird. Exemplary mammals include, but are not limited to rats, cats, dogs, horses, cows, sheep, pigs, and more preferably humans.

"Intranasal Delivery" as used herein, refers to the application, delivery and/or administration of at least one therapeutic agent or compound, at least one vasoconstrictor and/or a combination thereof, i.e., pharmaceutical composition, to the nasal cavity of the subject. Such intranasal delivery comprises application, delivery and/or administration of the compound(s), vasoconstrictor(s) and/or pharmaceutical composition to the entire nasal cavity, the upper one-third of the nasal cavity and/or the lower two-thirds of the nasal cavity. When upper one-third administration is preferred or required, it will be specified.

The present disclosure is generally directed to administering insulin intranasally to the upper one-third of a mammal's nasal cavity. An exemplary mammal is a human being. One of the objects of the present invention is to administer a treatment or preventative and/or mitigation therapy to lessen the severity, frequency and/or time of a steep blood glucose drop event to people suffering from, or at risk for, IAH.

In some embodiments, the therapeutic agent—insulin—may be combined with a vasoconstrictor to be administered intranasally to limit systemic exposure. The vasoconstrictor may be administered to the nasal cavity prior to administration of the therapeutic compound to the upper third of the nasal cavity or, alternatively, the vasoconstrictor and therapeutic compound may be administered concurrently. In any case, the effective amount of insulin will be administered to the upper third of the patient's nasal cavity, without exposure to the patient's non-CNS system, blood and/or organs.

Administration of intranasal insulin has been shown to improve memory in both normal adults and in patients with Alzheimer's disease. Recent studies have shown that insulin may enhance neuronal activity within the medio-temporal lobe and increase performance in humans under in-vivo conditions. The non-invasive intranasal method for bypassing the blood-brain barrier to target therapeutics (including insulin) to the brain to treat neurodegenerative disorders was first discovered by the inventor of the present disclosure, including the discovery, inter alia, applying intranasal insulin to the upper third of a patient's nasal cavity in order to target the CNS, e.g., brain, for treating and preventing Alzheimer's disease and certain other CNS disorders. Therapeutic agent(s) administered to the upper third of the patient's nasal cavity advantageously bypass the blood-brain barrier and rapidly reach the brain by traveling extracellularly along the olfactory and trigeminal neural pathways. This increases efficacy while reducing systemic exposure and unwanted side effects.

Intranasal insulin treatment improves memory in healthy adults with no change in the blood levels of insulin or glucose. For example, researchers in Germany have conducted several human clinical trials showing that intranasal insulin improves memory in normal adults. Intranasal insulin has been shown to improve memory in only twenty minutes after a single treatment in patients with Alzheimer's disease. Intranasal insulin has also been shown to improve memory, attention and functioning in Alzheimer's patients over a 21 day period, and improved memory and general cognition and reduced loss of brain FDG uptake in patients with Alzheimer's disease or amnestic mild cognitive impairment treated with intranasal insulin in a four month clinical trial with no change in the blood levels of insulin or glucose. It is noteworthy that the insulin in these studies was delivered generally intranasally, without specific targeting to the upper third of the patient's nasal cavity. Consequently, virtually all, i.e., in the range of 95% or greater, of the delivered insulin was administered to the lower two-thirds of the patient's nasal cavity and subsequently to the patient's system.

Insulin administered to the upper third of the nasal cavity can treat (lessen the severity of an ongoing event and/or shorten the time of the event) and prevent and/or mitigate (lessen severity and/or time of a future event and/or the frequencies of future events) of hypoglycemia events or episodes in patients suffering from IAH.

It is known that, in rodent models, central insulin signaling directly alters glucose sensing in hypothalamic neurons. Insulin delivered to the upper third of the nasal cavity as described herein will help to treat and/or prevent the neurocognitive changes associated with T1D including reductions in measures of motor speed and psychomotor efficiency seen in patients with T1D in midlife and thereafter. These neurocognitive changes have been associated with a reduction in white matter volume and/or an alternation in white matter microstructure. Reduction in gray matter density in brain regions responsible for language processing, memory and generalized atrophy have also been identified in young adults with long-standing T1D. The present invention may therefore prevent and/or treat these neurocognitive changes.

There are a variety of types of insulin available that may be used in accordance with the present disclosure, including insulins for which zinc is included for stabilization and others which do not include zinc. Because zinc may be detrimental to the olfactory system and may promote tau phosphorylation, insulins that do not contain zinc may be preferable in some cases. Formulations of insulin that either contain no preservatives (which could be prepared for unit dosing) or a safe preservative such as pyrophosphate are preferred. Acid sodium pyrophosphate is on the GRAS list for food additives and food preservatives. It is also sometimes referred to as disodium diphosphate and appears to bind metals such as iron and thus act as an antioxidant. In some embodiments the insulin formulation may not include any phenol or cresol preservatives.

The composition may include the neurologic agent (insulin) as well as a vasoconstrictor that may generally enhance the efficiency of delivery of the intranasally delivered therapeutic compound comprising insulin.

Thus, constriction of blood vessels resulting from action of the vasoconstrictor in the nasal cavity facilitates transport of the therapeutic compound(s) comprising insulin into the brain along olfactory and trigeminal neural pathways, perivascular pathways, or lymphatic pathways. Thus, intranasal administration of a therapeutic compound(s) comprising insulin to the upper one third of a patient's nasal cavity in combination with the intranasal administration of an agent that constricts blood vessels (i.e. a vasoconstrictor) within or in the proximity of the mucosa of the nasal cavity enhances targeting of the intranasally delivered insulin to the CNS by reducing absorption into the blood, increasing CNS concentrations (as well as other targeted locations), or both.

Therefore, in one embodiment, a pharmaceutical composition may comprise combination of at least one therapeutic compound comprising insulin and at least one vasoconstrictor. In another embodiment, at least one vasoconstrictor may be applied intranasally or otherwise, i.e., intravenously, topically as a pretreatment or concurrently with administration of at least one therapeutic compound. A vasoconstrictor may be applied before intranasal administration of the effective dose of insulin, or in a pharmaceutical composition with the insulin dose. The use of a vasoconstrictor may improve the efficiency of delivery of the intranasally administered insulin to the patient's CNS, regardless of whether the intranasal delivery is to the lower two-thirds or upper one-third of the patient's nasal cavity.

Exemplary vasoconstrictors in the various embodiments of the present invention may comprise, without limitation, PHE and/or THZ. Additional vasoconstrictors will be well known to the skilled artisan and may include, again without limitation, methoxamine, phenylephrine, ephedrine, norepinephrine, oxymatazoline, tetrahydrozoline, xylometazoline, clonidine, guanabenz, guanfacine, α-methyldopa, and/or arginine vasopressin.

An effective amount or dose as herein defined, of the therapeutic compound comprising insulin and/or vasoconstrictor to be administered pursuant to embodiments of the invention is the most preferred method of expression of dosage. Such effective amount is dependent upon many factors, including but not limited to, the type of disease or condition giving rise to an anticipated cerebral ischemia episode, the patient's general health, size, age, and the nature of the treatment, i.e. short-term or chronic treatment.

Generally, the treatment may be given in a single dose or multiple administrations, i.e., once, twice, three or more times daily over a period of time. As discussed herein, the dose may be administered immediately upon recognition of the onset of a hypoglycemia unawareness event and may be repeated as needed and described herein. Further, the administration of insulin to the upper third of the nasal cavity for patients at risk of events related to the steep glucose drop resulting from hypoglycemia unawareness may take preventive doses.

The method of the invention delivers the neurologic agent to the nasal cavity of a mammal; an exemplary and preferred mammal comprising a human being. In some embodiments, it is preferred that the insulin be delivered to the olfactory area in the upper third of the nasal cavity and particularly to the olfactory epithelium in order to promote transport of the agent along the peripheral olfactory axon bundles and into the perivascular channels to and throughout the CNS rather than into the capillaries within the respiratory epithelium. In some embodiments it may be preferable to transport insulin to the brain along the olfactory and trigeminal neural pathways instead of the circulatory system so that therapeutic agents that are unable to cross the blood-brain barrier from the bloodstream into the brain may be delivered to damaged neurons or neurons subject to damage in the brain.

To deliver the therapeutic compound comprising insulin to the CNS, at least one effective amount of the therapeutic compound comprising insulin either alone or in combination with at least one vasoconstrictor wherein the vasoconstrictor(s) may be used as a pretreatment or simultaneously administered with the effective amount of insulin, may be administered to the nasal cavity, most preferably to the upper third of the patient's nasal cavity, though the vasoconstrictor may be administered to the lower two-thirds of the nasal cavity. In the present invention, the therapeutic compound comprises insulin. If applied to the upper third of the nasal cavity, the vasoconstrictor and/or therapeutic compound comprising insulin, comprising in certain embodiments a pharmaceutical composition of the present invention, is applied to the respiratory epithelium of the nasal cavity or to the olfactory epithelium located in the upper one-third of the nasal cavity. In all cases of application and/or administration, the composition may be administered intranasally as a powder or liquid spray, nose drops, a gel, lipid emulsion, lipid nanoparticles, lipid nanospheres or ointment, through a tube or catheter, by syringe, packtail, pledget or by submucosal infusion.

The optimal concentration of the active therapeutic agent, i.e., therapeutic compound comprising insulin, as well as the concentration of the vasoconstrictor when used in various embodiments, will necessarily depend upon, inter alfa, the characteristics of the patient for which the insulin is being used and whether the dose is administered as part of a preventive treatment regimen or in response to an ongoing hypoglycemic event in the patient with IAH, though an effective amount is contemplated in all cases. Further, the stage of a particular disease or disorder, e.g., prevention vs. treatment of IAH, may dictate the optimal concentration of the therapeutic compound comprising insulin.

In another embodiment, at least one vasoconstrictor may be applied intranasally or otherwise, i.e., intravenously, topically as a pretreatment or concurrently with administration of an effective amount of at least one therapeutic compound comprising insulin. Further, an effective amount of at least one therapeutic compound comprising insulin may be combined with at least one vasoconstrictor to form a pharmaceutical compound that may be administered following pretreatment with intranasally (or intravenously, topically, etc.,) administered vasoconstrictor and/or concurrently with such vasoconstrictor.

Exemplary vasoconstrictors in the various embodiments of the present invention may comprise, without limitation, PHE and/or THZ. Additional vasoconstrictors will be well known to the skilled artisan and may include, again without limitation, methoxamine, phenylephrine, ephedrine, norepinephrine, oxymetazoline, tetrahydrozoline, xylometazoline, clonidine, guanabenz, guanfacine, α-methyldopa and/or arginine vasopressin.

An effective amount, as herein defined, of the therapeutic compound comprising insulin to be administered pursuant to embodiments of the invention is the most preferred method of expression of dosage. Such effective amount is dependent upon many factors, including but not limited to, the type of disease or condition, the patient's general health, size, age, and the nature of treatment, i.e., short-term of chronic treatment. For illustrative purposes only, exemplary treatment regimens relating generally to the therapeutic compounds comprising insulin disclosed herein, including dosage ranges, volumes and frequency are provided below, referencing the disclosure regarding effective amounts for the present invention described supra:

Efficacious dosage range: 0.0001-1.0 mg/kg.
A more preferred dosage range may be 0.002-1.0 mg/kg.
A further preferred dosage range may be 0.002-0.2 mg/kg.
A most preferred dosage range may be 0.002-0.1 mg/kg.
The dosage volume (applicable to nasal sprays or drops) range may be 0.015 mls-1.0 mls.
The preferred dosage volume (applicable to nasal sprays or drops) range may be 0.03-0.6 mls.
The efficacious vasoconstrictor dosage may be 0.0001-0.3 mg/kg.

The insulin may be administered in a dose comprising an effective amount of insulin as defined above. Such effective amounts may include for example, 0.1 IU, 1 IU, 5 IU, 10 IU, 20 IU, 40 IU, or more. We may assume a specific activity of 27 units/mg for insulin generally. Thus, 40 units is the equivalent of approximately 1.5 mg. We further assume an average adult weighs about 75 kg, which results a dosing of approximately 0.02 mg/kg dose. Other trials and studies have administered 20 units, which, using the above assumption criteria, would be about 0.01 mg/kg dose. Still other trials and studies have used 10 units or about 0.005 mg/kg.

Generally, the treatment may be given in a single dose (as a treatment for an ongoing event) or multiple administrations, i.e., once, twice, three or more times daily over a period of time. For patients at highest risk of hypoglycemia unawareness events, a preventive treatment regimen may consist of at least one dose per day over an extended period of time.

The brain concentrations that are likely to be achieved with the dosage ranges provided above are, for a single dose: 0.1 nM-50 μM. Over the course of a multi-dose treatment plan, the maximum brain concentration may be as high as 500 μM.

As described above, the neurologic agent—insulin— alone or in a composition may be administered intranasally as a powder, spray, gel, ointment, infusion, injection, or drops through a tube or catheter, by syringe, by packtail, by pledget, or by submucosal infusion. Any suitable nasal spray device targeting the upper third of the patient's nasal cavity may be used with embodiments of the present disclosure.

It will be understood, however, that any particular effective amount as defined above is contemplated and within the scope of the present disclosure. Doses of the effective amount of insulin may be administered immediately for example, from about one minute to about 120 minutes and any specific point there between following onset of conditions related to hypoglycemia unawareness, and/or from about one minute to about 120 minutes and any specific point thereafter. It will be understood that the disclosed times of about 1 to about 120 minutes pre- or post- a hypoglycemia unawareness event are not intended to be limiting and that doses may be administered at any useful time point before and/or after an event including less than a minute and greater than 120 minutes. The effective amount, including inter alia dosage volumes are discussed in further detail infra.

The present invention should not be considered limited to the particular examples described above, but rather should be understood to cover all aspects of the invention. Various modifications, equivalent processes, as well as numerous structures to which the present invention may be applicable will be readily apparent to those of skill in the art to which the present invention is directed upon review of the present specification.

What is claimed is:

1. A method for treating patients with impaired awareness of hypoglycemia (IAH), comprising:
   identifying a patient with IAH;
   providing at least one effective amount of a therapeutic compound comprising an insulin;
   administering the at least one effective amount of the therapeutic compound comprising the insulin to the upper one-third of the nasal cavity of the patient, thereby enabling the administered at least one effective amount of the therapeutic compound comprising the insulin to bypass the patient's blood-brain barrier;
   directly delivering the at least one effective amount of the therapeutic compound comprising the insulin to the patient's central nervous system (CNS); and
   mitigating the unawareness of hypoglycemia in the patient with IAH.

2. The method of claim 1, wherein the therapeutic compound comprising the insulin does not contain zinc.

3. The method of claim 2, wherein the insulin is glulisine.

4. The method of claim 1, further comprising administering a vasoconstrictor to the patient.

5. The method of claim 1, wherein the therapeutic compound comprising the insulin further comprises pyrophosphate for preservation and wherein the therapeutic compound is prepared for unit dosing to administer the at least one effective amount.

6. The method of claim 1, wherein the therapeutic compound comprising the insulin does not contain a cresol or a phenol preservative and wherein the therapeutic compound is prepared for unit dosing to administer the at least one effective amount.

7. The method of claim 1, wherein the at least one effective amount of the insulin is within the range of 0.0001-1.0 mg/kg.

8. The method of claim 7, wherein a dosage range for the therapeutic compound comprising the insulin is within the range of 0.002-0.1 mg/kg.

9. The method of claim 7, wherein a dosage range for the therapeutic compound comprising the insulin is within the range of 0.03-0.6 mls.

10. The method of claim 1, wherein the at least one effective amount of the insulin is within the range of 0.002-0.2 mg/kg.

11. The method of claim 1, wherein administration of the at least one effective amount of the therapeutic compound comprising the insulin results in a brain concentration of the insulin in the range of 0.1 nM-50 µM.

* * * * *